(12) United States Patent
Granger et al.

(10) Patent No.: US 6,949,247 B2
(45) Date of Patent: Sep. 27, 2005

(54) STABLE SKIN CARE COMPOSITIONS CONTAINING A RETINOID AND A RETINOID BOOSTER SYSTEM

(75) Inventors: Stewart Paton Granger, Paramus, NJ (US); Prem Chandar, Closter, NJ (US); Ian Richard Scott, Allendale, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 207 days.

(21) Appl. No.: 10/008,067

(22) Filed: Nov. 5, 2001

(65) Prior Publication Data

US 2003/0049286 A1 Mar. 13, 2003

Related U.S. Application Data

(60) Provisional application No. 60/258,459, filed on Dec. 28, 2000.

(51) Int. Cl.$^7$ .............................. A61K 6/00; A61K 7/42; A61K 31/07
(52) U.S. Cl. ........................... 424/401; 424/59; 514/725
(58) Field of Search .................... 424/401, 59; 515/725

(56) References Cited

U.S. PATENT DOCUMENTS

| | | | |
|---|---|---|---|
| 5,034,228 A | | 7/1991 | Meybeck et al. |
| 5,536,730 A | | 7/1996 | Suzuki et al. |
| 5,536,740 A | * | 7/1996 | Granger et al. |
| 5,583,136 A | | 12/1996 | Yusuf et al. |
| 5,665,367 A | | 9/1997 | Burger et al. |
| 5,716,627 A | * | 2/1998 | Granger et al. |
| 5,747,051 A | * | 5/1998 | Granger et al. |
| 5,756,109 A | | 5/1998 | Burger et al. |
| 5,800,596 A | | 9/1998 | Collin et al. |
| 5,976,555 A | * | 11/1999 | Liu et al. |

FOREIGN PATENT DOCUMENTS

| | | |
|---|---|---|
| EP | 0 742 005 A2 | 11/1996 |
| EP | 0 803 247 A2 | 10/1997 |
| EP | 0 803 248 A2 | 10/1997 |
| FR | 2 777 194 A1 | 10/1999 |
| WO | 93/19743 | 10/1993 |
| WO | 96/07396 | 3/1996 |
| WO | 97/31620 | 9/1997 |
| WO | 98/13020 | 2/1998 |
| WO | WO 98/13020 * | 4/1998 |
| WO | 01/09000 A1 | 2/2001 |
| WO | 01/30314 A1 | 5/2001 |
| WO | 02/02074 A2 | 1/2002 |

OTHER PUBLICATIONS

J. C. Saari & K. L. Bredberg, "CoA and Non–CoA Dependent Retinol Esterification in Retinal Pigment Epithelium", *J. Bill. Chem.* 263, 8084–8090 (1988).
J. C. Saari & D. L. Bredberg, "ARAT & LRAT Activities of Bovine Retinal Pigment Epithelial Microsomes", *Methods Enzymol.* 190, 156–163 (190).
J. L. Napoli & K. R. Race, "The Biosynthesis of Retinoic Acid from Retinol by Rat Tissues in Vitro", *Archives Biochem. Biophys.* 255, 95–101 (1987).
R. Martini & M. Murray, "Participation of P450 3A Enzymes in Rat Hepatic Microsomal Retinoic Acid 4–Hydroxylation", *Archives Biochem. Biophys.* 303, 57–66 (1993).
A. B. Barua, "Analysis of Water–Soluble Compounds: Glucuronides", *Methods Enzymol.* 189, 136–145 (1990).
A.W. Norris, E. Li, "Generation and Characterization of Cellular Retinoic Acid–binding Proteins from *Escherichia Coli* Expressions Systems." *Methods Enzymol.* 282, 3–13 (1997).
Vahlquist,A. et al., "Isotretinoin Treatment of Severe Acne Affects the Endogenous Concentration of Vitamin A in Sebaceous Glands", *J. Invest. Dermatol.*, vol. 94, Holland D.B. and Cunliffe, W.J. (1990), pp. 496–498.
Charles N. Ellis, J.J. Voorhees, "Treatment of Actinically Aged Skin with Topical Tretinoin", S. Karger, Basel, *Pharmacology and the Skin*, vol. 3, 249–252 (1989).
Partial International Search Report No. PCT/EP 01/14491 mailed Dec. 11, 2002, 6 pp.
International Search Report No. PCT/EP 01/14491 mailed Jan. 21, 2003—10 pp.

* cited by examiner

Primary Examiner—Shengjun Wang
(74) Attorney, Agent, or Firm—Ellen Plotkin

(57) ABSTRACT

A stable skin care composition containing about 0.0001% to about 50% of at least one retinoid booster, about 0.001% to about 10% of a retinoid; and a cosmetically acceptable vehicle, wherein the stable skin care composition is contained in a package so that the composition is out of contact with oxygen.

6 Claims, No Drawings

STABLE SKIN CARE COMPOSITIONS CONTAINING A RETINOID AND A RETINOID BOOSTER SYSTEM

This application claims priority of provisional application No. 60/258,459, filed on Dec. 28, 2000.

FIELD OF INVENTION

The invention relates to stable skin care compositions containing a retinoid and a retinoid booster system contained in packages so that the compositions are out of contact with oxygen.

BACKGROUND OF THE INVENTION

Retinoids (e.g. retinol and retinyl esters) are common ingredients used in cosmetic products. Retinol (vitamin A) is an endogenous compound which occurs naturally in the human body and is essential for normal epithelial cell differentiation. Natural and synthetic vitamin A derivatives have been used extensively in the treatment of a variety of skin disorders and have been used as skin repair or renewal agents. Retinoic acid has been employed to treat a variety of skin conditions, e.g., acne, wrinkles, psoriasis, age spots and discoloration. See e.g. Vahlquist, A. et al., *J. Invest. Dermatol.*, Vol. 94, Holland D. B. and Cunliffe, W. J. (1990), pp. 496–498; Ellis, C. N. et. Al., "Treatment of Actinically Aged Skin with Tropical Tretinoin," *S. Karger, Basel* Vol. 3, (1989), pp. 249–252; and PCT Patent Application No. WO 93/19743.

Retinol, however, is particularly unstable in cosmetic formulations because retinol can undergo chemical degradation as a consequence of many factors which include oxidation, thermal instability and UV induced degradation. Retinyl esters are also subject to these instabilities although to a lesser extent than retinol. Retinoid benefits on skin can be enhanced by the coapplication of retinoid booster molecules. However, many if not all of the retinoid booster molecules also increase the instability of the retinol. It is necessary therefore to protect retinol formulations containing boosters to a higher degree than is necessary for formulations containing retinol alone.

Several references seek to create stable compositions containing retinol. For example, U.S. Pat. No. 5,976,555 assigned to Johnson & Johnson, discloses skin care compositions comprising oil in water emulsions containing retinoids, an emulsifier system, and a co-emulsifier. The patent describes the use of a container for storing the composition so that the composition is out of contact with oxygen. The container is described for use for the retinoid composition with an emulsifier system and a co-emulsifier alone and does not protect the retinoid from degradation due to contact with retinoid boosters.

U.S. Pat. No. 5,800,596, assigned to L'Oreal, discloses a water in oil emulsion containing retinol in a dispensing device that has walls impermeable to oxygen or UV light and an oxygen trapping device. The patent does not teach or suggest the use of boosters and the problems associated with retinoid stability in the presence of boosters.

None of the references cited above teach or suggest systems for stabilizing retinoid compositions in the presence of retinoid boosters. Therefore, a need still exists for such stable cosmetic compositions containing retinoids and retinoid boosters.

SUMMARY OF THE INVENTION

A stable skin care composition containing:

about 0.0001% to about 50% of at least one retinoid booster;

about 0.001% to about 10% of a retinoid; and a cosmetically acceptable vehicle, wherein the stable skin care composition is contained in a package so that the composition is out of contact with oxygen.

As used herein, the term "comprising" means including, made up of, composed of, consisting and/or consisting essentially of. Except in the operating and comparative examples, or where otherwise explicitly indicated, all numbers in this description indicating amounts or ratios of material or conditions of reaction, physical properties of materials and/or use are to be understood as modified by the word "about".

DETAILED DESCRIPTION OF THE INVENTION

The inventive compositions contain, as a preferred ingredient, a retinoid, which is selected from retinyl esters, retinol, retinal and retinoic acid, preferably retinol or retinyl ester. The term "retinol" includes the following isomers of retinol: all-trans-retinol, 13-cis-retinol, 11-cis-retinol, 9-cis-retinol, 3,4-didehydro-retinol, 3,4-didehydro-13-cis-retinol; 3,4-didehydro-11-cis-retinol; 3,4-didehydro-9-cis-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. The term "retinol" has been defined above. Retinyl esters suitable for use in the present invention are $C_1$–$C_{30}$ esters of retinol, preferably $C_2$–$C_{20}$ esters, and most preferably $C_2$, $C_3$, and $C_{16}$ esters because they are more commonly available. Examples of retinyl esters include but are not limited to: retinyl palmitate, retinyl formate, retinyl acetate, retinyl propionate, retinyl butyrate, retinyl valerate, retinyl isovalerate, retinyl hexanoate, retinyl heptanoate, retinyl octanoate, retinyl nonanoate, retinyl decanoate, retinyl undecanoate, retinyl laurate, retinyl tridecanoate, retinyl myristate, retinyl pentadecanoate, retinyl heptadeconoate, retinyl stearate, retinyl isostearate, retinyl nonadecanoate, retinyl arachidonate, retinyl behenate, retinyl linoleate, retinyl oleate.

The preferred ester for use in the present invention is selected from retinyl palmitate, retinyl acetate and retinyl propionate, because these are the most commercially available and therefore the cheapest. Retinyl linoleate and retinyl oleate are also preferred due to their efficacy.

Retinol or retinyl ester is employed in the inventive composition in an amount of about 0.001% to about 10%, preferably in an amount of about 0.01% to about 1%, most preferably in an amount of about 0.01% to about 0.5%.

It is believed that retinoids are enzymatically converted in the skin into retinoic acid according to the mechanism described in Chart 1.

Retinol metabolism in the epidermis: enyme names

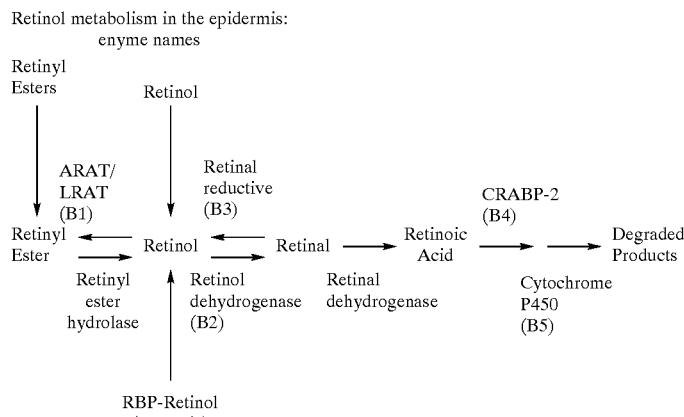

ARAT/LRAT = Acyl Coenzyme A (CoA): Retinol Acyl Transferase/Lecithin: Retinol Acyl Transferase CRABPII = Cellular Retinoic Acid Binding Protein II It has been discovered, surprisingly, that certain compounds inhibit ARAT/LRAT, retinal reductase, CRABPII and retinoic acid oxidation (the latter catalyzed by cytochrome P450 systems), whereas certain other compounds enhance retinol dehydrogenase. The compounds are collectively termed herein as "boosters" and are coded as groups B1 through B5, as can be seen in Chart 1 hereinabove. The boosters, alone or in combination with each other, potentiate the action of a retinoid by increasing the amount of retinol available for conversion to retinoic acid and inhibiting the degradation of retinoic acid. The boosters act in conjunction with a retinoid (e.g. retinol, retinyl ester, retinal, retinoic acid), the latter being present endogenously in the skin. The preferred compositions, however, include a retinoid in the composition, co-present with a booster, to optimize performance.

The present invention includes, in part, a second composition containing about 0.0001% to about 50%, preferably about 0.001% to about 10%, most preferably about 0.001% to about 5%, by weight of the composition of at least one booster compound, wherein the compound, either alone or at a combined concentration of 10 mM inhibit transglutaminase in an in vivo transglutaminase assay to more than 50%, and a cosmetically acceptable vehicle.

The boosters included in the inventive compositions are selected from the group consisting of:
(a) Two boosters, wherein both are selected from the same group consisting of B2; B3; B4;
(b) binary combinations of boosters selected from the group consisting of
B1/B2; B1/B3; B1/B4; B1/B5; B2/B3, B2/B4; B2/B5, B3/B4; B3/B5; B4/B5
(c) ternary combinations of boosters selected from the group consisting of
B1/B2/B3; B1/B2/B4; B1/B2/B5; B1/B3/B4; B1/B3/B5; B1/B4/B5; B2/B3/B4; B2/B4/B5; B3/B4/B5
(d) quaternary combinations of boosters selected from the group consisting of
B1/B2/B3/B4; B1/B2/B3/B5; B1/B2/B4/B5; B1/B3/B4/B5; B2/B3/B4/B5; and
(e) a combination of five groups of boosters: B1/B2/B3/B4/B5.

The preferred compositions include at least one booster from the different groups (i.e., groups (b) through (e) above).

However, any combination of boosters chosen from the different groups may also be employed in the inventive compositions for desired boosting effects.

The compounds included in the present invention as boosters are first selected based on the ability of such compounds to pass, at a certain concentration listed in Table A, an in-vitro Microsomal Assay for a specific enzyme as described below under sections 2.1 through 2.7. The compound (alone or in combination with another booster) is then subjected to an in vitro transglutaminase assay described below, at an individual or combined concentration of 10 mM. If such combination inhibits transglutaminase to more than 50%, then it is suitable for use in the present invention. If a booster was tested individually, and passes the transglutaminase assay, then it may be combined with another booster or combination that passes the transglutaminase assay.

Preferred compositions according to the present invention contain combinations of booster which at an individual concentration of 10 mM inhibit transglutaminase to more than 50%.

The term "conditioning" as used herein means prevention and treatment of dry skin, acne, photodamaged skin, appearance of wrinkles, age spots, aged skin, increasing stratum corneum flexibility, lightening skin color, controlling sebum excretion and generally increasing the quality of skin. The composition may be used to improve skin desquamation and epidermal differentiation.

A booster is a compound which passes an in vitro Microsomal Assay described below in sections 2.1 through 2.7. A compound suitable for use in the present invention inhibits or enhances at a concentration listed in Table A, an enzyme, to at least a broad % listed in Table A.

TABLE A

| Booster Test Concentrations and % Inhibition/Increase | | |
|---|---|---|
| ARAT/LRAT Assay (To identify B1 boosters) | | |
| Invention | Compound Concentration | % Inhibition |
| Broad | 100 µM | >10% |
| Preferred | 100 µM | >25% |

TABLE A-continued

Booster Test Concentrations and % Inhibition/Increase

| | | |
|---|---|---|
| Most Preferred | 100 μM | >40% |
| Optimum | 100 μM | >50% |

Retinol Dehydrogenase Assay (To identify B2 boosters)

| Invention | Compound Concentration | % Inhibition |
|---|---|---|
| Broad | 100 μM | >10% |
| Preferred | 100 μM | >15% |
| Most Preferred | 100 μM | >20% |
| Optimum | 100 μM | >25% |

Retinal Reductase Assay (To identify B3 boosters)

| Invention | Compound Concentration | % Inhibition |
|---|---|---|
| Broad | 100 μM | >5% |
| Preferred | 100 μM | >10% |
| Most Preferred | 100 μM | >20% |
| Optimum | 100 μM | >35% |

CRABPII Antagonist Assay (To identify B4 boosters)

| Invention | Compound:RA Ratio | % Inhibition |
|---|---|---|
| Broad | 7000:1 | >25% |
| Preferred | 7000:1 | >50% |
| Most Preferred | 70:1 | >25% |
| Optimum | 70:1 | >50% |

Retinoic Acid Oxidation Assay (To identify B5 boosters)

| Invention | Compound Concentration | % Inhibition |
|---|---|---|
| Broad | 100 μM | >25% |
| Preferred | 100 μM | >45% |
| Most Preferred | 100 μM | >70% |
| Optimum | 100 μM | >80% |

The in vitro Microsomal Assays employed for determining the suitability of the inclusion of the compound in the inventive compositions are as follows:

1. Materials

All-trans-retinol, all-trans-retinoic acid, palmitoyl-CoA, dilauroyl phosphatidyl choline, NAD, and NADPH were purchased from Sigma Chemical Company. Stock solutions of retinoids for the microsomal assays were made up in HPLC grade acetonitrile. All retinoid standard stock solutions for HPLC analysis were prepared in ethanol, stored under atmosphere of N2 at −70° C. and maintained on ice under amber lighting when out of storage. Other chemicals and the inhibitors were commercially available from cosmetic material suppliers or chemical companies such as Aldrich or International Flavors and Fragrances.

2. Methods 2.1 Isolation of RPE Microsomes (Modified from J. C. Saari & D. L. Bredberg, "CoA and Non-CoA Dependent Retinol Esterification in Retinal Pigment Epithelium", *J. Bill. Chem.* 263, 8084–8090 (1988)).

50 frozen hemisected bovine eyecups, with the retina and aqueous humor removed were obtained from W. L. Lawson Co., Lincoln, Nebr., USA. The eyes were thawed overnight and the colored iridescent membrane was removed by peeling with forceps. Each eyecup was washed with 2×0.5 mL cold buffer (0.1M PO4/1 mM DTT/0.25M sucrose, pH 7) by rubbing the darkly pigmented cells with an artist's brush or a rubber policeman. The cell suspension was added to the iridescent membranes and the suspension was stirred for several minutes in a beaker with a Teflon stir bar. The suspension was filtered through a coarse filter (Spectra/Por 925μ pore size polyethylene mesh) to remove large particles, and the resulting darkly colored suspension was homogenized using a Glas-Col with a motor driven Teflon homogenizer. The cell homogenate was centrifuged for 30 min. at 20,000 g (Sorvaal model RC-5B centrifuge with an SS34 rotor in 2.5×10 cm tubes at 14,000 RPM). The resulting supernatant was subjected to further centrifugation for 60 min. at 150,000 g (Beckman model L80 Ultracentrifuge with an SW50.1 rotor in 13×51 mm tubes at 40,000 RPM). The resulting pellets were dispersed into ~5 mL 0.1M PO4/5 mM DTT, pH 7 buffer using a Heat Systems Ultrasonics, Inc. model W185D Sonifier Cell Disruptor, and the resulting microsomal dispersion was aliquoted into small tubes and stored at −70° C. The protein concentrations of the microsomes were determined using the BioRad Dye binding assay, using BSA as a standard.

2.2 Isolation of Rat Liver Microsomes (R. Martini & M. Murray, "Participation of P450 3A Enzymes in Rat Hepatic Microsomal Retinoic Acid 4-Hydroxylation", *Archives Biochem. Biophys.* 303, 57–66 (1993)).

Approximately 6 grams of frozen rat liver (obtained from Harlan Sprague Dawley rats from Accurate Chemical and Scientific Corp.) were homogenized in 3 volumes of 0.1M tris/0.1M KCl/1 mM EDTA/0.25M sucrose, pH 7.4 buffer using a Brinkmann Polytron. The resulting tissue suspension was further homogenized in the motor driven Teflon homogenizer described above. The resulting homogenate was successively centrifuged for 30 min. at 10,000 g, 30 min. at 20,000 g, and 15 min. at 30,000 g, and the resulting supernatant was ultracentrifuged for 80 min. at 105,000 g. The pellet was sonicated in ~5 mL of 0.1M PO$_4$/0.1 mM EDTA/5 mM MgCl2, pH 7.4 buffer as described above and stored as aliquots at −70° C. Protein concentrations were determined as described above.

2.3 Assay for ARAT and LRAT activity (To Identify B1)

The procedure below is a modification of a method described in J. C. Saari & D. L. Bredberg, "ARAT & LRAT Activities of Bovine Retinal Pigment Epithelial Microsomes", *Methods Enzymol.* 190, 156–163 (1990). The following buffer was prepared and stored at 4° C.: 0.1M PO$_4$/5 mM dithiothreitol, pH 7.0 (PO$_4$/DTT). On the day of the assay, add 2 mg BSA per mL of buffer to give a PO$_4$/DTT/BSA working buffer. 1 mM retinol substrate was prepared in acetonitrile and stored in amber bottles under nitrogen gas at −20° C. Solutions of 4 mM Palmitoyl-CoA in working buffer (stored in aliquots) and 4 mM dilauroyl phosphatidyl choline in ethanol were prepared and stored at −20° C. Inhibitors were prepared as 10 mM stock solutions in H2O, ethanol, acetonitrile or DMSO. The quench solution was prepared using pure ethanol containing 50 μg/mL butylated hydroxytoluene (BHT), and a hexane solution containing 50 μg/mL BHT was used for the extractions.

To a 2 dram glass vial, add the following in order: PO$_4$/DTT/BSA buffer to give a total volume of 500 μL, 5 μL acyl donor (4 mM palmitoyl-CoA and/or dilauroyl phosphatidyl choline), 5 μL inhibitor or solvent blank (10 mM stock or further dilutions) followed by approximately 15 μg of RPE microsomal protein (approximately 15 μL of a ~1 mg/mL microsomal protein aliquot). Incubate for 5 min. at 37° C. to equilibrate the reaction temperature and then add 5 μL 1 mM retinol. Cap the vials, vortex for 5 seconds and incubate for 30–90 minutes at 37° C. Quench the reaction by adding 0.5 mL ethanol/BHT. Extract the retinoids by adding 3 mL hexane/BHT, vortex the tubes for several seconds several times and centrifuge the tubes at low speed for 5 min. to quickly separate the layers. Remove the upper hexane layer into a clean vial, and re-extract the aqueous layer with another 3 mL hexane/BHT, as described above. Combine the hexane layers and evaporate the hexane by drying at 37° C. under a stream of nitrogen gas on a heated aluminum block. Store the dried residue at −20° C. until HPLC analysis. Quantitate the amount of retinyl palmitate and retinyl laurate for ARAT and LRAT activity, respectively, by integration of the HPLC signal as described below.

Note that the incubation solution contains 40 µM acyl donor, 100 µM or less inhibitor, 10 µM retinol, approximately 30 µg/mL microsomal protein, and nearly 0.1M $PO_4$, pH 7/ 5 mM DTT/2 mg/mL BSA. All steps subsequent to the addition of retinol were done in the dark or under amber lights.

2.4 Assay for Retinol Dehydrogenase Activity (To Identify B2)

The following stock solutions were prepared:
50 mM $KH_2PO_4$, pH 7.4 buffer, sterile filtered.
10 mM all trans Retinol (Sigma R7632) in DMSO.
200 mM Nicotinamide adenine dinucleotide phosphate, sodium salt (NADP) (Sigma N0505) in sterile water.
40 mM test compound in appropriate solvent (water, buffer, ethanol, chloroform or DMSO).
1:10 dilution of rat liver Microsomes in 50 mM $KH_2PO_4$, pH7.4 buffer (4 micro g/micro l).

In a two-dram glass vial with screw cap, add the following in order:
Buffer to give a final volume of 400 µl
25 µl diluted Microsomes (final=100 µg)—use boiled Microsomes for controls and regular Microsomes for test samples.
4 µl of 200 mM NADP (final=2 mM)
1 µl of 40 mM test compound (final=100 µM)
8 µl of 10 mM retinol (final=200 µM)

Incubate vials in a 37° C. shaking water bath for 45 minutes. Add 500 µl ice-cold ethanol to each vial to quench the reaction. Extract the retinoids twice with ice cold hexane (2.7 ml per extraction). Retinyl acetate (5 µl of a 900 µM stock) is added to each vial during the first extraction as a means of monitoring the extraction efficiency in each sample. Samples were vortexed for ten seconds before gently centrifuging for five minutes at 1000 rpm, 5° C. in a Beckman GS-6R centrifuge. The top hexane layer containing the retinoids is removed from the aqueous layer after each extraction to a clean two-dram vial. Evaporate off the hexane under a gentle stream of nitrogen gas. Store the dried residue at −20° C. until HPLC analysis.

2.5 Assay for Retinal Reductase Activity (To Identify B3)

All stock solutions were prepared as above with the following substitutions:
10 mM all trans Retinaldehyde (Sigma R2500) in DMSO—instead of retinol.
200 mM, Nicotinamide adenine dinucleotide phosphate, reduced form, tetrasodium salt (NADPH) (Sigma N7505) in sterile water—instead of NADP.

In a two-dram glass vial with screw cap, add the following in order:
Buffer to give a final volume of 400 µl
25 µl diluted Microsomes (final=100 µg)—use boiled Microsomes for controls and regular Microsomes for test samples.
4 µl of 200 mM NADPH (final=2 mM)
1 µl of 40 mM test compound (final=100 µM)
3 µl of 10 mM retinaldehyde (final=75 µM)

Follow the same incubation and extraction procedure as detailed above.

2.6 Assay for CRABPII Antagonists (To Identify B4)

2.6.1. Synthesis of CRABPII a. System of Expression

The gene CRABPII was cloned in pET 29a–c(+) plasmid (Novagen). The cloned gene was under control of strong bacteriophage T7 transcription and translation signals. The source of T7 polymerase was provided by the host cell *E.coli* BLR(DE3)pLysS (Novagen). The latter has a chromosomal copy of T7 polymerase under lacUV5 control, induced by the presence of IPTG. The plasmid was transferred into *E. coli* BLR(DE3)pLysS cells by transformation according to the manufacturer protocol (Novagen).

b. Induction

An overnight culture of the transformed cells was diluted 1:100 into 2×YT containing 50 µg/mL kanamycin and 25 µg/mL chloramphenicol. The cells grew while shaking at 37° C. until the OD at 600 nm reached 0.6–0.8. Then IPTG was added to a final concentration of 1 mM and the culture was incubated for an additional two hours. The cells were harvested by centrifugation at 5000 g for 10 minutes at room temperature. The pellet was stored at −20° C.

2.6.2. Purification

Purification was performed according to the method described in Norris, A. W., Li, E. "Generation and characterization of cellular retinoic acid-binding proteins from *Escherichia coli* expression systems", *Methods Enzymol.*, 282, 3–13 (1997).

a. Lysis

The frozen pellet was thawed at RT and resuspended in 1–2 pellet volumes of freshly prepared lysis buffer (50 mM Tris-Hcl, pH 8, 10%(w/v) sucrose, 1 mM EDTA, 0.05%(w/v) sodium azide, 0.5 mM DTT, 10 mM $MnCl_2$, 2.5 mM phenylmethylsulfonyl fluoride, 2.5 mM benzamidine, 6 µg/mL DNase). The lysate was incubated for 30 min at room temperature. Further lysis was accomplished by sonication (six 30-sec bursts at 10,000 psi alternated with five 30-sec delay on ice). The insoluble fraction of the lysate was removed by centrifugation at 15000 rpm 1 hour at 4° C. and the supernatant is stored at −20° C.

b. Gel Filtration on Sephacryl S300

The supernatant from step a. was loaded onto a 2.5×100 cm column of sephacryl S-300 (Pharmacia) at room temperature. The elution buffer was 20 mM Tris-HCl, pH 8, 0.5 mM DTT, 0.05% sodium azide (buffer A). The flow rate was 2 mL/min. Collected 2-mL fractions were checked for ultraviolet absorbance at 280 nm. The fractions representing the peaks were examined by SDS-page for the presence of CRABPII.

c. Anion-exchange Chromatography 2 mL of gel filtration fractions containing CRABPII were loaded onto a quaternary amine anion-exchange column FPLC (Fast Protein Liquid Chromatography) type monoQ (Pharmacia). CRABPII was eluted using a gradient buffer from 100% buffer A to 30% buffer B (100% buffer B=buffer A+250 mM NaCl) over a 20-min period at room temperature. 1 mL-fractions were collected every minute. Once more, the presence of CRABPII was checked by SDS page. CRABPII was stored at 4° C. before freeze-drying using a Micromodulyo 1.5K with vial platform attachment (Edwards High Vacuum International). The desiccated samples were stored at room temperature until their use in the binding assay.

d. Detection of the Presence of CRABPII

The expression and purification of CRABPII was validated using denaturing SDS-polyacrylamide gel electrophoresis (SDS-PAGE) analysis on a 7–15% polyacrylamide gel (Biorad). 10 μL samples were mixed with 10 μL of 2× loading buffer (100 mM Tris-HCl pH6.8, 4% SDS, 0.2% BPB, 20% glycerol, 1 mM DTT) and denatured by heating (2 min at 80° C.). The samples were loaded onto the gel that was immersed in a 1× Tris-glycine buffer (Biorad) and a constant current (25 mA) was applied for 1 hour at room temperature. After Coomassie blue staining, the protein was identified according to its molecular weight as determinated with the Benchmark prestained protein ladder (Gibco BRL).

A western blot was used to confirm the presence of CRABPII. The proteins separated on the SDS-PAGE were transferred on an Immobilon-P transfer membrane (Millipore) using a Biorad cassette. The transfer occurred in 1× Tris-glycine buffer (Biorad)+10% methanol. An electrical current (60 mA) was applied for 3 hours to allow the protein to migrate through the membrane. Afterwards, the membrane was blocked with 5% dry milk in 1×TBS for one hour at room temperature and probed with primary antibodies to CRABPII (1/1000 dilution of mouse anticlonal 5-CRA-B3) in the same buffer at 4° C. overnight. The following day, the membrane was washed with PBS (3×5 minutes) and then incubated with 1:2000 dilution of the secondary antibody, peroxidase conjugated anti-mouse antibody (ECLTM, Amersham), for 1 hour at room temperature. The membrane was washed with 1×PBS (3×5 minutes) and the protein was detected using ECL detection kit according to the manufacturer instruction (Amersham).

The concentration of purified CRABPII was determined using BSA kit (Pierce).

2.6.3. Radioactive Binding Assay 220 pmol of CRABPII was incubated in 20 mM Tris-HCl buffer pH 7.4 with 15 pmol of radioactive all trans retinoic acid (NEN) in a total volume of 70 μL. For the competitive assay, another ligand in excess (6670:1, 670:1 or 70:1) was added to the mix. The reaction occured for one hour at room temperature in the dark. In order to separate the unbound all-trans retinoic acid from the bound all-trans retinoic acid, a 6 kD cut-off minichromatography column (Biorad) was used. The storage buffer was discarded using a Microplex manifold for according to the manufacturer instruction (Pharmacia). The samples were loaded onto the column and the separation occured by gravity over a 30-min period. Retinoic acid ("RA") bound to CRABPII appeared in the filtrate while free RA remained in the column. The radioactivity of the filtrate was measured by scintillation counter.

2.7 Assay for NADPH Dependent Retinoic Acid Oxidation (To Identify B5)

The procedure below is a modification of a method described in R. Martini & M. Murray, "Participation of P450 3A Enzymes in Rat Hepatic Microsomal Retinoic Acid 4-Hydroxylation", *Archives Biochem. Biophys.* 303, 57–66 (1993). Prepare the following assay buffer and store at 4° C.: 0.1M $PO_4$/0.1 mM EDTA/5 mM $MgCl_2$, pH 7.4. On the day of the assay, prepare a 60 mM NADPH solution in buffer. Prepare inhibitor stocks, acidified ethanol/BHT quench solution, and hexane/BHT as described above. A working 1 mM retinoic acid solution was prepared by dilution of a 15 mM stock (in DMSO) with ethanol.

To a 2 dram vial, add the following in order: assay buffer to give a final volume of 500 μL, 20 μL 60 mM NADPH, 5 μL inhibitor or solvent blank, followed by approximately 2 mg of rat liver microsomal protein. Incubate for 5 min. at 37° C., then add 5 μL working 1 mM retinoic acid solution. Continue incubation for 60 min. at 37° C.—do not cap the vials, since the oxidation process requires molecular oxygen in addition to NADPH. Quench with acidified ethanol/BHT and extract with hexane/BHT as described above. Quantitate the quickly eluting polar retinoic acid metabolites (presumed to be 4-oxo retinoic acid) by integration of the HPLC signal, as described below.

Note that all steps subsequent to the addition of retinoic acid were done in the dark or under amber lights. The final incubation solution contains 2.4 mM NADPH, 100 μM or less inhibitor, 10 μM retinoic acid, approximately 4 mg/mL rat liver microsomal protein and nearly 0.1M $PO_4$/0.1 mM EDTA/5 mM $MgCl_2$.

HPLC Analysis of Individual Retinoids

Samples for retinoid quantitation by HPLC were prepared by dissolving the residue in each vial with 100 μL of methanol. The solution was transferred to a 150 μL glass conical tube within a 1 mL shell vial, capped tightly, and placed inside a Waters 715 Autosampler. Aliquots of 60 μL were injected immediately and analyzed for retinoid content.

The chromatography instrumentation consisted of a Waters 600 gradient controller/pump, a Waters 996 Photodiode Array detector and a Waters 474 Scanning Fluorescence detector. Two HPLC protocols were used for retinoid analysis. For the ARAT and LRAT assay, the separation of retinol and retinol esters was performed with a Waters 3.9×300 mm C18 Novapak reverse-phase analytical column and Waters Sentry NovaPak C18 guard column with an 80:20(v/v) methanol/THF is isocratic mobile phase adjusted to a flow rate of 1 mL/min. for 10 min. The eluate was monitored for absorbance at 325 nm and fluorescence at 325 ex/480 em. A shorter Waters 3.9×150 mm C18 Novapak reverse-phase analytical column and Waters Sentry Nova-Pak C18 guard column were used to separate retinoid acids and alcohols for the retinol and retinoic acid oxidation assays utilizing a modification of a gradient system described by A. B. Barua, "Analysis of Water-Soluble Compounds: Glucuronides", *Methods Enzymol.* 189, 136–145 (1990). This system consisted of a 20 min. linear gradient from 68:32(v/v) methanol/water containing 10 mM ammonium acetate to 4:1(v/v) methanol:dichloromethane followed by a 5 min. hold at a flow rate of 1 mL/min. The column eluate was monitored from 300 nm to 400 nm.

These protocols were selected based on their ability to clearly resolve pertinent retinoid acids, alcohols, aldehydes, and/or esters for each assay and relative quickness of separation. Identification of individual retinoids by HPLC was based on an exact match of the retention time of unknown peaks with that of available authentic retinoid standards and UV spectra analysis (300–400 nm) of unknown peaks against available authentic retinoids.

The boosters suitable for further testing in the transglutaminase assay include but are not limited to the boosters listed in Tables B1 through B5 below.

| | | ARAT/LRAT Inhibitors (B1) | | | | | |
|---|---|---|---|---|---|---|---|
| Class | Compound | % Inhibition Overall TG (−ROH/RE) | Overall TG (IC 50) | % Inhibition ARAT (10 μm) | % Inhibition ARAT (100 μm) | % Inhibition LRAT (10 μm) | % Inhibition LRAT (100 μm) |
| Carotenoid | Crocetin | | 3.75E−05 | 15% | 34% | 0 | 15% |
| Fatty Acid Amides & Other Surfactants | Acetyl Sphingosine | | 6.78E−06 | 19% +/− 12 | 62% +/− 11 | 10% +/− 10 | 50% +/− 18 |
| Fatty Acid Amides & Other Surfactants | C13 Beta-Hydroxy Acid/Amide | 17% | | | 28% | | 25% |
| Fatty Acid Amides & Other Surfactants | Castor Oil MEA | | 3.25E−05 | | | | |
| Fatty Acid Amides & Other Surfactants | Cocamidopropyl Betaine | | | | 25% | | |
| Fatty Acid Amides & Other Surfactants | Coco Hydroxyethylimidazoline | | 2.84E−07 | | 68% | | 68% |
| Fatty Acid Amides & Other Surfactants | Cocoamide-MEA (or Cocoyl Monoethanolamide) | 11% | | | 13% | | 34% |
| Fatty Acid Amides & Other Surfactants | Glycerol-PCA-Oleate | | | | 41% +/− 6 | | 58% +/− 2 |
| Fatty Acid Amides & Other Surfactants | Hexanoamide | | | | 20% | | |
| Fatty Acid Amides & Other Surfactants | Hexanoyl Sphingosine | | 9.99E−05 | | 28% +/− 4 | | 37% +/− 9 |
| Fatty Acid Amides & Other Surfactants | Hydroxyethyl-2-Hydroxy-C12 Amide | | 3.29E−05 | | 35% | | 35% |
| Fatty Acid Amides & Other Surfactants | Hydroxyethyl-2-Hydroxy-C16 Amide | | | | 25% | | 30% |
| Fatty Acid Amides & Other Surfactants | Lauroyl Sarcosine | | | | 20% | | |
| Fatty Acid Amides & Other Surfactants | Lidocaine | | | | 12% | | 0 |
| Fatty Acid Amides & Other Surfactants | Linoleamide-DEA (or Linoleoyl Diethanolamide) | 59% | | 12% +/− 13 | 43% +/− 3 | 11% +/− 9 | 51% +/− 15 |
| Fatty Acid Amides & Other Surfactants | Linoleamide-MEA (or Linoleoyl Monoethanolamide) | | 1.61E−05 | 14% | 35% | 20% +/− 8 | 35% |
| Fatty Acid Amides & Other Surfactans | Linoleamidopropyl Dimethylamine | | | | 69% +/− 18 | | 75% +/− 4 |
| Fatty Acid Amides & Other Surfactants | Melinamide | | | | 64% +/− 15 | | 43% +/2 21 |
| Fatty Acid Amides & Other Surfactans | Myristoyl Sarcosine | | | | 41% +/− 14 | | 11% +/− 11 |
| Fatty Acid Amides & Other Surfactants | Oleyl Betaine | | 2.80E−05 | | 47% | | |
| Fatty Acid Amides & Other Surfactants | Palmitamide-MEA | | | 6% | 23% | 12% | 33% |
| Fatty Acid Amides & Other Surfactants | Stearylhydroxyamide | | | | 10% | | 10% |
| Fatty Acid Amides & Other Surfactants | Utrecht-1 | 21% | | 43% | 54% | 51% | 48% +/− 6 |
| Fatty Acid Amides & Other Surfactants | Utrecht-2 | | 3.47E−06 | 42% | 83% +/− 9 | 51% | 92% +/− 3 |
| Flavanoids | Naringenin | | | | 33% | | 14% |
| Fragrances | Allyl Alpha-Ionone | | | 16% +/− 14 | 22% +/− 23 | 17% +/− 10 | 36% /− 7 |
| Fragrances | Alpha-Damascone | | 3.35E−04 | 67% +/− 27 | 83% +/− 12 | 87% +/− 6 | 98% +/− 1 |
| Fragrances | Alpha = Ionone | | 9.27E−04 | | 45% +/− 27 | | 49% +/− 30 |
| Fragrances | Alpha-Methyl Ionone | | | | 67% | | 77% |
| Fragrances | Alpha-Terpineol | | | | 26% | | 25% |
| Fragrances | Beta-Damascone | | | 45% | 84% | 52% | 92% |
| Fragrances | Brahmanol | | | | 70% | | 75% |
| Fragrances | Damascenone | | | 23% | 70% | 29% | 79% |
| Fragrances | Delta-Damascone | | | 58% | 87% | 64% | 95% |
| Fragrances | Dihydro Alpha-Ionone | | | | 13% | | 18% |
| Fragrances | Ethyl Saffranate | | | | 51% | | 49% |
| Fragrances | Fenchyl Alcohol | | | | 12% | | 4% |
| Fragrances | Gamma-Methyl Ionone | | | | 21% | | 38% |
| Fragrances | Isobutyl Ionone | | | | 8% | | 45% |
| Fragrances | Isocyclogeraniol | | | | 18% | | 16% |
| Fragrances | Isodamascone | | | | 80% | | 92% |
| Fragrances | Lyral | | 1.27E−04 | | 76% | | 71% |
| Fragrances | Santalone | | | | 23% | | 12% |
| Fragrances | Santanol | | | | 15% | | 43% |
| Fragrances | Timberol | | | | 34% | | 33% |
| Fragrances | Tonalid | | | | 50% | | 33% |
| Fragrances | Traseolide | | | | 41% | | 21% |
| Miscellaneous | Coco Trimethylammonium Cl- | | | | 27% | | |
| Miscellaneous | Urosolic Acid | | 1.46E−06 | | 21% | | 28% |

ARAT/LRAT Inhibitors (B1)

| Class | Compound | % Inhibition Overall TG (−ROH/RE) | Overall TG (IC 50) | % Inhibition ARAT (10 μm) | % Inhibition ARAT (100 μm) | % Inhibition LRAT (10 μm) | % Inhibition LRAT (100 μm) |
|---|---|---|---|---|---|---|---|
| Noncyclic Fragrances | Citral | | | | 20% | | |
| Noncyclic Fragrances | Citronellol | | | | 30% | | 0 |
| Noncyclic Fragrances | Farnesol | | 9.35E−05 | 23% +/− 18 | 53% +/− 18 | 10% +/− 7 | 53% +/− 19 |
| Noncyclic Fragrances | Geraniol | | 7.83E−03 | 13% | 32% | | |
| Noncyclic Fragrances | Geranyl Geraniol | | | 38% +/− 12 | 81% +/− 6 | 16% +/− 9 | 77% +/− 13 |
| Noncyclic Fragrances | Linatool | | | | 28% | | 0 |
| Noncyclic Fragrances | Nonadieneal | | | | 20% | | |
| Noncyclic Fragrances | Pseudoionone | | | | 12% | | 37% |
| Phospholipid | Dioctylphosphatidyl Ethanolamine | | | 23% | 50% +/− 2 | 0 | 17% +/− 17 |
| Urea | Dimethyl Imidazolidinone | 22% | | | | | |
| Urea | Imidazolidinyl Urea | 35% | | | | | |

Retinol Dehydrogenase Activators (B2)

| Class | Compound | % Increase Retinol Dehydrogenase |
|---|---|---|
| Phospholipid | Phosphatidyl Choline | 21% increase |
| Phospholipid | Sphingomyelin | 26% increase |

Retinaldehyde Reductase Inhibitors (B3)

| Class | Compound | Overall TG (IC 50) | % Inhibition Retinal Reductase |
|---|---|---|---|
| Aldehyde | Vanillin | 9.70E−03 | 6% |
| Fatty Acid | Arachidic Acid | | 20% |
| Fatty Acid | Arachidic Acid | | 49% |
| Fatty Acid | Linoleic Acid | 1.63E−04 | 62% +/− 2 |
| Fatty Acid | Linolenic Acid | 1.34E−04 | 54% +/− 16 |
| Fatty Acid | Myristic Acid | 1.72E−05 | 26% |
| Miscellaneous | Amsacrine | 6.26E−06 | 22% +/− 8 |
| Miscellaneous | Carbenoxolone | 3.61E−07 | 26% +/− 2 |
| Miscellenous | Glycyrretinic Acid | 8.64E−06 | 38% =/− 1 |
| Phospholipid | Phosphatidyl ethanolamine | | 37% |

CRABPII Antagonists (B4)

| Class | Compound | Overall TG (IC 50) | % Inhibition CRABPII |
|---|---|---|---|
| Fatty Acid | Elaidic Acid | 6.50E−05 | >50% |
| Fatty Acid | Hexadecanedioic Acid | 1.30E−04 | >50% |
| Fatty Acid | 12-Hydroxystearic Acid | 2.91E−05 | >50% |
| Fatty Acid | Isostearic Acid | 6.88E−05 | >50% |
| Fatty Acids | Linseed Oil | | >50% |

Retinoic Acid Oxidation Inhibitors (B5)

| Class | Compound | Overall TG (IC 50) | % Inhibition Retinoic Acid (10 μM) | % Inhibition Retinoic Acid (100 μM) |
|---|---|---|---|---|
| Imidazole | Bifonazole | | 89% | 100% |
| Imidazole | Climbazole | 4.47E−06 | 80% | 92% |
| Imidazole | Clotrimazole | | 76% | 85% |
| Imidazole | Econazole | | 88% | 100% |
| Imidazole | Ketoconazole | 1.85E−07 | 84% | 84% |
| Imidazole | Miconazole | 2.78E−07 | 74% | 86% |
| Fatty Acid Amides & Other Sufactants | Lauryl Hydroxyethylimidazoline | 4.67E−07 | | |
| Fatty Acid Amides & Other Sufactants | Oleyl Hydroxyethylimidazoline | 3.02E−05 | 54% | 80% |
| Flavanoids | Quercetin | 6.29E−05 | 40% | 74% |
| Coumarin | Coumarin | | | |
| Quinoline | (7H-Benzimidazo[2, 1-a]Benz[de]-Isoquinolin-7-one | 8.59E−07 | | |

-continued

| | Retinoic Acid Oxidation Inhibitors (B5) | | | |
|---|---|---|---|---|
| Class | Compound | Overall TG (IC 50) | % Inhibition Retinoic Acid (10 μM) | % Inhibition Retinoic Acid (100 μM) |
| Quinoline | Hydroxyquinoline (Carbostyril) | 3.64E−04 | | |
| Quinoline | Metyrapone (2-Methyl-1, 2-di-3-Pyridyl-1-Propane) | | | 47% |

The boosters or combinations thereof inhibit transglutaminase (hereinafter "Tgase") in a transglutaminase assay described below to at least 50% at a concentration of 10 mM.

| TGase Assay | | |
|---|---|---|
| Invention | Compound Concentration | % Inhibition |
| Broad | 10 mM | >50% |
| Preferred | 1 mM | >50% |
| Most Preferred | 100 μM | >50% |
| Optimum | 10 μM | >50% |

Transglutaminase Assay and Keratinocyte Differentiation

During the process of terminal differentiation in the epidermis, a 15 nm thick layer of protein, known as the cornified envelope (CE) is formed on the inner surface of the cell periphery. The CE is composed of numerous distinct proteins which have been cross-linked together by the formation of $N^\epsilon$-($\gamma$-glutamyl) lysine isodipeptide bonds catalyzed by the action of at least two different transglutaminases (TGases) expressed in the epidermis. TGase I is expressed in abundance in the differentiated layers of the epidermis, especially the granular layer, but is absent in the undifferentiated basal epidermis. Thus TGase I is a useful marker of epidermal keratinocyte differentiation with high TGase I levels indicating a more differentiated state. An ELISA based TGase I assay, using a TGase I antibody, was used to assess the state of differentiation of the cultured keratinocytes in the examples that follow.

Keratinocytes (cultured as described above) were plated in 96 well plates at a density of 4,000–5,000 cells per well in 200 μl media. After incubation for two to three days, or until cells are ~50% confluent, the media was changed to media containing test compounds (five replicates per test). The cells were cultured for a further 96 hours after which time the media was aspirated and the plates stored at −70° C. Plates were removed from the freezer, and the cells were washed twice with 200 μl of 1×PBS. The cells were incubated for one hour at room temperature (R/T) with TBS/5% BSA (wash buffer, bovine serum albumin). Next the TGase primary antibody was added: 50 μl of monoclonal anti-Tgase I Ab B.C. diluted 1:2000 in wash buffer. The primary antibody was incubated for 2 hours at 37° C. and then rinsed 6× with wash buffer. Cells were then incubated with 50 μl of secondary antibody (Fab fragment, peroxidase conjugated anti-mouse IgG obtaining from Amersham) diluted 1:4,000 in wash buffer for two hours at 37° C., then rinsed three times with wash buffer. Following the rinse with washing buffer, the cells were rinsed 3× with PBS. For colourimetric development, the cells were incubated with 100 μl substrate solution (4 mg o-phenylenediamine and 3.3 μl 30% $H_2O_2$ in 10 ml 0.1 M citrate buffer pH 5.0) for exactly five minutes, R/T, in darkness (under aluminum foil). The reaction was stopped by the addition of 50 μl 4N $H_2SO_4$. The absorbance of samples was read at 492 nm in a 96 well plate UV spectrophotometer. Out of the five replicates, four were treated with both antibodies, the fifth one was use as a Tgase background control. TGase levels were determined and expressed as percentage control.

Transglutaminase levels were determined and expressed in the Tables B1 through B5 above either as:

(i) % (booster+retinol inhibition/control inhibition)−% (ROH inhibition/control inhibition), which measures the added effect of booster+retinol induced TGase inhibition over retinol alone, or or (ii) as an IC50 value when the inhibitory effect of multiple booster concentrations was examined—this provides the concentration of booster which, in combination with a constant retinol concentration of $10^{-7}$M, inhibits TGase by 50%.

It is the IC50 value that is used as a benchmark in the present invention.

Best Groups of Boosters for Testing in Transglutaminase Assay

| | B1 Compounds | |
|---|---|---|
| 1. | Fatty Acid Amides | These are readily commercially available and have the added advantage of being surfactants and thus help generate emulsions suitable for cosmetic preparations. |
| 2. | Ceramides | These can additionally act as precursors of stratum corneum barrier ceramides. |
| 3. | Carotenoids | These can offer some UV protection and and act as natural colorants. |
| 4. | Flavonoids | Natural antioxidants. |
| 5. | Cyclic fragrances | These are readily commercially available and additionally can be used to fragrance the product. |
| 6. | Non-cyclic fragrances | These can be used to fragrance the product. |

-continued

| B1 Compounds | |
|---|---|
| 7. Phospholipid analogues | These can be utilised by skin cells to nourish the generation of barrier components. |
| 8. Ureas | These are readily commercially available and can also act as preservatives for the product. |

| B2 Compounds | |
|---|---|
| 1. Phosphatidyl choline | Most preferred as most active activator of Retinol Dehydrogenase |
| 2. Sphingomyelin | |

| B3 Compounds | |
|---|---|
| Arachidonic Acid | Fatty Acids which can be useful in maintaining stratum corneum barrier |
| Linoleic Acid | |
| Linolenic Acid | |
| Myristic Acid | |
| Linoleic Acid | Essential Fatty Acids |
| Linolenic Acid | |
| Arachidonic Acid | Non-essential fatty acids |
| Myristic Acid | |
| Glycyrrhetinic Acid | Polycyclic triterpene carboxylic acid which is readily obtained from plant sources. |
| Phosphatidyl ethanolamine | Can be incorporated into cellular membranes. |

| B4 Compounds | |
|---|---|
| Hexadecanedioic acid | Saturated fatty acids. |
| 12-hydroxystearic acid | |
| Isostearic acid | |
| Linseed oil | Unsaturated fatty acids |
| Elaidic acid | |
| Elaidic acid | Solid at room temperature |
| Isostearic acid | |
| Hexadecanedioic acid | |
| Linseed oil | Liquid at room temperature |
| 12-hydroxystearic acid | |

| B5 Compounds | |
|---|---|
| Bifonazole | Antimicotics |
| Climbazole | |
| Clotrimazole | |
| Econazole | |
| Ketoconazole | |
| Miconazole | |
| Climbazole | Readily commercially available |
| Lauryl hydroxyethylimidazoline | Compounds which are readily commercially available and have the added advantage of being surfactants and thus help generate emulsions suitable for cosmetic preparations. |
| Quercetin | Naturally occuring flavanoid which has antioxidant properties. |
| Coumarin | Natural colorant |
| Quinolines | |
| Isoquinolines | |
| Metyrapone | |

Minimal Oxygen Permeable Package

As discussed hereinabove, compositions which include retinoids are generally unstable and may undergo chemical degradation. Moreover, it has been surprisingly found that boosters, although beneficial for enhancing the retinoid benefits, also contribute to the chemical instability of retinoids. The booster induced retinol destabilization dramatically reduces the overall efficacy of the boosted retinoid system when both ingredients are contained in a single formula. Therefore, there is a need to protect retinoid compositions in formulations containing boosters from breakdown to a higher degree than is needed for compositions with retinoids alone. Specifically, it is necessary to create stable compositions with retinoids and retinoid boosters to provide the beneficial boosting effects of retinoid boosters while preventing retinoid degradation before the boosting effect can occur. Therefore, the present invention provides a package that is minimally oxygen permeable to stabilize the retinoid and booster composition, thereby minimizing the booster induced degradation of retinoids.

The minimal oxygen permeable package can be constructed in various methods known to persons of ordinary skill in the art. Specifically, the inventive compositions should not be in direct contact with oxygen or air, and oxygen should be prevented from seeping through the outer walls of the package. Packages which are opaque to light and impermeable to oxygen may be used. For example, aluminum may be used for the walls of the package, or as lining inside the package.

Cosmetically Acceptable Vehicle

The product according to the present invention also comprises a cosmetically acceptable vehicle to act as a dilutant, dispersant, or carrier for the active components in the either or both the first and second compositions, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 centistokes at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5 to 95%, preferably from 25 to 90% by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Various types of active ingredients may be present in the cosmetic compositions of the present invention and are described below. Actives are defined as skin or hair benefit agents other than emollients and other than ingredients that merely improve the physical characteristics of the composition. Although not limited to this category, general examples include sunscreens, skin lightening agents, tanning agents.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively.

The exact amount of sunscreen employed in the emulsions can vary depending upon the degree of protection desired from the sun's UV radiation.

Another preferred optional ingredient is selected from essential fatty acids (EFAs), i.e., those fatty acids which are essential for the plasma membrane formation of all cells, in keratinocytes EFA deficiency makes cells hyperproliferative. Supplementation of EFA corrects this. EFAs also enhance lipid biosynthesis of epidermis and provide lipids for the barrier formation of the epidermis. The essential fatty acids are preferably chosen from linoleic acid, γ-linolenic acid, homo-γ-linolenic acid, columbinic acid, eicosa-(n-6,9, 13)-trienoic acid, arachidonic acid, γ-linolenic acid, timnodonic acid, hexaenoic acid and mixtures thereof.

Emollients are often incorporated into cosmetic compositions of the present invention. Levels of such emollients may range from about 0.5% to about 50%, preferably about 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts of about 0.1 to about 20% by weight, preferably about 0.5% to about 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic compositions of the present invention. These powders include chalk, talc, Fullers earth, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the compositions of the present invention. These ingredients may include coloring agents, opacifiers and perfumes. Amounts of these materials may range from 0.001% to 20% by weight of the composition.

The compositions of the present invention are intended primarily as a product for topical application to human skin, especially as an agent for conditioning and smoothening the skin, and preventing or reducing the appearance of wrinkled or aged skin.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a fluid cream, a cream or a gel.

EXAMPLE 1

Methods

Retinol (50% in tween 80) was dissolved in approximately 50% aqueous ethanol to provide a solution giving an OD at 360 nm of approximately 0.6 when measured in a 200 μl volume in a 96 well plate using a standard 96 well spectrophotometer.

Booster molecules were added at approximately 0.1% concentration and the OD 360 measured as above immediately and after 60 hours at room temperature in the dark. A correction was applied to the OD after 60 hours (divide by 0.85) to account for increased concentration of the retinol due to evaporation of solvent from the plate.

Results

| BOOSTER | FOLD INCREASE IN RATE OF RETINOL LOSS |
|---|---|
| CITRAL | 3.1 |
| CITRONELLOL | 1.5 |
| COCAMIDE DEA | 1.9 |
| COUMARIN | 1.4 |
| DAMASCONE | 3.7 |
| 1,3 DIMETHYL 2 IMIDAZOLIDINONE | 1.4 |
| GERANIOL | 1.3 |
| 18 b GLYCERHETINIC ACID | 1.6 |
| 8 OH QUINOLINE | 1.5 |
| N LAURY SARCOSINE | 2.6 |
| LINALOOL | 2.0 |
| LINOLEAMIDE DEA | 3.0 |
| LINOLEIC ACID | 3.4 |
| ALPHA IONONE | 1.3 |
| LINSEED OIL | 1.5 |

The Boosters tested caused marked increases in the instability of the retinol.

This will make it necessary to use formulation/packaging options providing considerably better stability to the retinol when boosters are used compared to those needed for retinol alone.

EXAMPLE 2

To establish whether synergistic inhibition of transglutaminase expression occurred by combinations of B1 and B5 active compounds with retinol, it is essential to determine the dose response profiles (including IC50 values) of the active compounds when tested individually in the presence of retinol. This data was used to determine an appropriate sub-maximal inhibitory concentration of each active compound, to make it possible to identify synergistic effects of mixtures of the active compounds in the presence of retinol. In order to demonstrate synergy of two compounds, it is essential to select concentrations to test that are at most IC20, in other words a compound concentration that individually boosts the retinol inhibition of transglutaminase expression by 20%. Two such compounds should have an additive inhibition of 40%. Using this strategy to determine concentration leaves a window of 40–100% for further transglutaminase inhibition for detecting synergy of the two compounds under examination. A more challenging concentration criteria would be selecting concentrations of compounds which alone showed no boosted retinol inhibition of transglutaminase. In this study, however, even more challenging criteria were chosen. Concentrations of compounds that were 10 fold and 100 fold lower than the minimally effective transglutaminase inhibiting concentration were selected. Identification of synergistic combinations using such very low concentrations would mean that the most effective synergistic combinations were identified.

The data in the following table represents the concentrations of compound that are 2 logs lower than the minimally inhibitory compound concentration. These were the concentrations used in the B1/B5 combination studies.

TABLE 1

| Compound | Concentration |
|---|---|
| B1 Compounds | |
| Linoleoyl monoethanolamide | 1.00E−06 |
| Palmitamide monoethanolamide | 1.00E−06 |
| Farnesol | 3.16E−06 |
| Hexyl sphingosine | 1.00E−06 |
| Utrecht-2 | 3.16E−08 |
| Oleoyl betaine | 3.16E−07 |
| Oleoyl hydroxyethylimidazoline | 1.00E−08 |
| Cocoyl hydroxyethylimidazoline | 1.00E−09 |
| Ursolic acid | 1.00E−08 |
| Alpha-ionone | 3.16E−05 |
| B5 Compounds | |
| Ketoconazole | 1.00E−09 |
| Miconazole | 3.16E−09 |
| Climbazole | 1.00E−08 |
| Amino benzotriazole | 1.00E−06 |
| 3,4-dihydroquinoline | 1.00E−06 |
| 2-hydroxyquinoline | 3.16E−06 |

To investigate synergistic inhibition of transglutaminase expression by combinations of B1 and B5 active compounds with retinol, selected combinations of compounds were tested at concentrations given in the above table. The following data was obtained:

TABLE 2

| Combination | B1 Compound | B5 Compound | Mean % control TGase |
|---|---|---|---|
| B1/B5 | Farnesol | Ketoconazole | 84% |
| B1/B5 | Hexanoyl sphingosine | Miconazole | 68% |
| B1/B5 | Hexanoyl sphingosine | Ketoconazole | 64% |
| B1/B5 | Hexanoyl sphingosine | 3,4-dihydroquinoline | 89% |
| B1/B5 | Hexanoyl sphingosine | Aminobenzotriazole | 81% |
| B1/B5 | Hexanoyl sphingosine | Climbazole | 63% |
| B1/B5 | Oleoyl betaine | Ketoconazole | 81% |
| B1/B5 | Oleoyl hydroxyethylimidazoline | Climbazole | 52% |
| B1/B5 | Cocoyl hydroxyethylimidazoline | Climbazole | 71% |
| B1/B5 | Ursolic acid | 2-hydroxyquinoline | 74% |
| B1/B5 | Alpha-ionone | Miconazole | 84% |
| B1/B5 | Alpha-ionone | Ketoconazole | 82% |
| B1/B5 | Alpha-ionone | 2-hydroxyquinoline | 76% |
| B1/B5 | Utrecht-2 | aminobenzotriazole | 82% |
| B1/B5 | Linoleoyl monoethanolamide | Ketoconazole | 93% |

TABLE 2-continued

| Combination | B1 Compound | B5 Compound | Mean % control TGase |
|---|---|---|---|
| B1/B5 | Linoleoyl monoethanolamide | Climbazole | 94% |
| B1/B5 | Naringenin | Ketoconazole | 100% |
| B1/B5 | Quercetin | Climbazole | 92% |
| B1/B5 | Castor Oil monoethanolamide | Climbazole | 98% |
| B1/B5 | Castor Oil monoethanolamide | Clotrimazole | 100% |

The efficacy of the B1/B5 combinations splits into two classes—particularly effective combinations (bolded in the above table i.e., the first 14 combinations) and barely effective combinations (not bolded i.e., the last six combinations). It was unexpected that certain B1/B5 combinations performed better than other combinations. Those combinations which were barely effective were (i) fatty acid amides+azoles (ii) hydroxy fatty acid amides+azoles and (iii) naringenin/quercetin+azoles. The effective combinations contained B1 boosters combined with B5 boosters from the following classes: fatty hydroxyethyl imidazoline surfactants, cyclic aliphatic unsaturated compounds, polycyclic triterpenes, n-substituted fatty acid amides.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as described and claimed herein, and that the inventions be limited only by the scope of the claims which follow, and that such claims be interpreted as broadly as is reasonable. Throughout this application, various publications and books have been cited. The entireties of each of these publications and books are hereby incorporated by reference herein.

What is claimed is:

1. A stable skin care composition containing:

about 0.00001% to about 50% of alpha-ionone;

optionally, about 0.00001% to about 50% of at least one retinoid booster selected from the group consisting of citral, cocomide DEA, coumarin, 1,3-dimethyl 2 imidazolidinone, geraniol, 8 OH quinoline, N laury sarcosine, linoleamide DEA, linoleic acid, linseed oil;

about 0.0001% to about 50% of at least one retinoid booster selected from the group consisting of ketoconazole, miconazole, 2-hydroxyquinoline, and combination thereof;

about 0.001% to about 10% of a retinoid selected from the group consisting of retinyl esters, retinol, retinal, and mixtures thereof; and a cosmetically acceptable vehicle, wherein the stable skin care composition is contained in a package so that the composition is out of contact with oxygen; and wherein said package is made out of aluminum; thereby alleviating additional retinoid instability contributed by said boosters.

2. A method of conditioning skin, the method comprising applying topically to the skin the composition of claim 1.

3. A method of mimicking the effect on skin of retinoic acid, the method comprising applying to the skin the composition of claim 1.

4. The stable skin care composition of claim 1, wherein said retinoid is present in an amount of about 0.01% to about 1%.

5. The stable skin care composition of claim 1, further comprising about 0.5% to about 50% of an emollient selected from the group consisting of esters, fatty acids, alcohols, polyols, and hydrocarbons.

6. The stable skin care composition of claim 1 wherein the composition has at least three boosters in an amount of from about 0.0001% to about 50%, wherein the composition of claim 1 further comprises at least one retinoid booster selected from the group consisting of geranyl geraniol, farnesol, acetamide AMEA, palmitamide AMEA, brahmanol, and mixtures thereof.

* * * * *